United States Patent [19]
Felix et al.

[11] Patent Number: 4,747,843
[45] Date of Patent: May 31, 1988

[54] CONTROL MODULE FOR THORACIC DRAINAGE APPARATUS

[75] Inventors: Augustus Felix, Providence; John Uhoch, Warwick, both of R.I.

[73] Assignee: C.R. Bard, Inc., Murray Hill, N.J.

[21] Appl. No.: 863,925

[22] Filed: May 15, 1986

[51] Int. Cl.⁴ .............................................. A61M 1/00
[52] U.S. Cl. ................................... 604/318; 604/319
[58] Field of Search ................. 137/205; 604/318–321

[56] References Cited

U.S. PATENT DOCUMENTS

| | | | |
|---|---|---|---|
| 4,396,386 | 8/1983 | Kurtz et al. | 604/318 |
| 4,519,796 | 5/1985 | Russo | 604/319 |
| 4,544,370 | 10/1985 | Elliot et al. | 604/319 |

*Primary Examiner*—C. Fred Rosenbaum
*Assistant Examiner*—J. L. Kruter
*Attorney, Agent, or Firm*—Wolf, Greenfield & Sacks

[57] ABSTRACT

A control module for regulating the flow of gases in a suction drainage apparatus. The drainage apparatus includes a collection container in communication with a body cavity to receive body fluids (including liquids and gases) therefrom and a suction source for creating a negative pressure within the collection container and removing the gases of the body fluids. The control module includes a serial arrangement of chambers and a plurality of flow control means in a unitary compact structure which fits within a recess provided in the collection container. The control module is adapatable to different sizes and types of collection means and does not add appreciably to the overall size of the device. Baffle means are provided to prevent the loss of the indicator liquid from the air leak indicator means if the device is tipped in any direction.

12 Claims, 8 Drawing Sheets

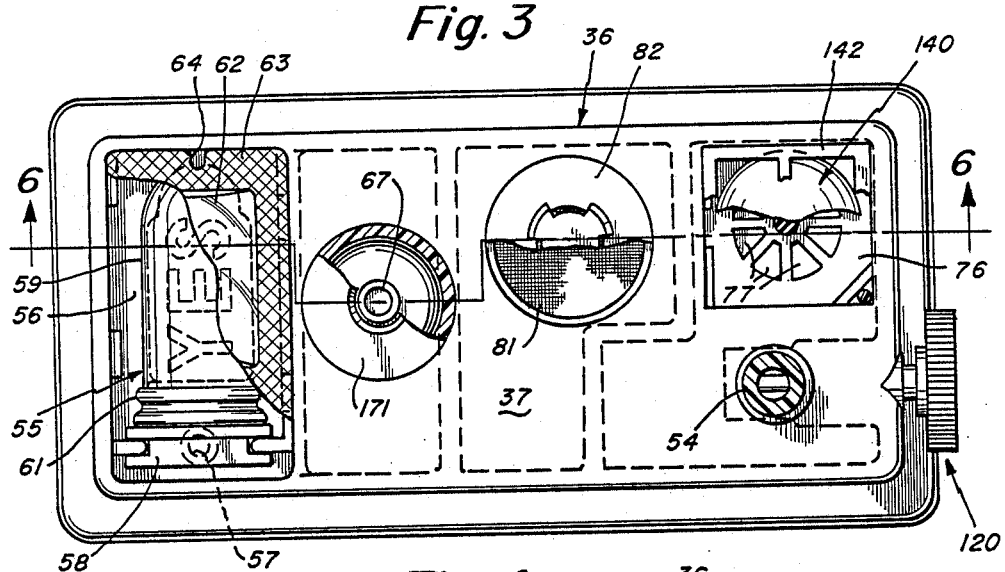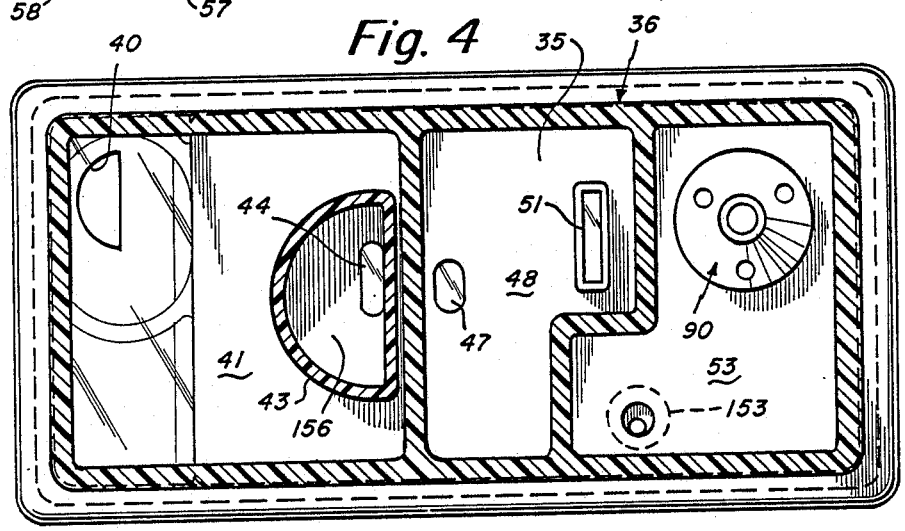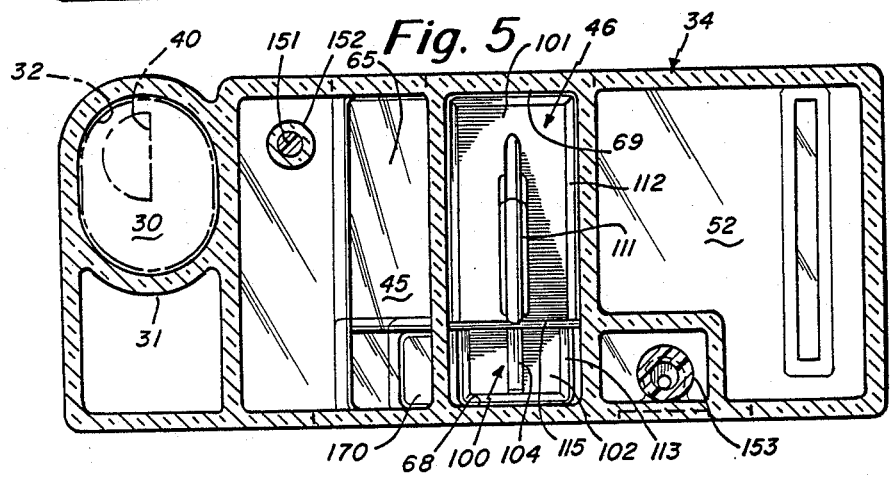

CONTROL MODULE FOR THORACIC DRAINAGE APPARATUS

BACKGROUND OF THE INVENTION

This invention relates to thoracic drainage apparatus of the type including a collection chamber and a suction source, and more particularly to a control module for regulating the removal of gases from the collection chamber to the suction source.

Various types of thoracic drainage devices have been developed for draining fluids from the pleural cavity of a human being into a collection chamber maintained at a negative pressure. The principal function of a thoracic drainage device is to evacuate gases and liquids from the pleural cavity in order to restore the normally negative intrapleural pressure and permit proper expansion of the patient's lungs. To accomplish this, the device must include a one-way seal which permits gases to flow out of the pleural cavity and into the drainage device but which prevents the return of any gases from the drainage device toward the pleural cavity. Two types of one-way seals have been used, an underwater seal and a one-way mechanical seal (e.g., umbrella valve).

In addition to a one-way seal, thoracic drainage devices include other means for regulating the flow of gases through the device. See, for example, U.S. Pat. Nos. 4,544,370 to Elliott et al., 4,468,226 to Kurtz et al., and 4,465,483 to Weilbacher. A suction control regulator is provided to control the amount of suction applied by the suction source to the collection chamber. An indicator means is provided to show the level of applied suction. A positive pressure relief means is provided to relieve any positive pressure buildup in the device when the patient coughs or in the event of a system malfunction. A negative pressure relief means is provided to relieve any excess negative pressure caused, for example, by a sharp inspiration or by stripping the patient tube leading from the pleural cavity to the collection chamber. A liquid-filled U-tube or air leak indicator is provided through which the gases exiting the pleural cavity can be observed as they bubble through the liquid.

Thoracic drainage devices are widely used in ambulatory care and thus such devices should be compact, easy to handle, nonbreakable, and their operation should not be affected if inclined or tilted. For transportation on a bedrail, the device should be of a reduced height.

It would be desirable to provide a thoracic drainage device in modular form wherein the modular components can be combined to produce a number of different size and type drainage devices. Previous attempts to produce a modular thoracic drainage device are shown in U.S. Pat. Nos. 3,847,152 to Schachet, 4,439,190 to Protzmann et al., and 4,465,483 to Weilbacher; see also the modular urine discharge measuring system shown in U.S. Pat. No. 4,448,207 to Parrish. In these known modular thoracic drainage devices, the various system components, such as the collection chamber, the one-way seal means, the pressure regulating means, etc., are formed as separate modular components which can be connected together to form a modular unit. None of these prior art devices is significantly more compact or adaptable and each has many more connections between components and thus an increased risk of air leakage.

SUMMARY OF THE INVENTION

The apparatus of the present invention satisfies the foregoing requirements of size, adaptability, portability, and leak-proof assembly. It consists of a modular control unit for a suction drainage apparatus that includes all of the necessary regulatory components in a single compact unit, is adaptable to fit a variety of collection containers, and can be nested within an external recess in the collection container. The control module is connectable in airtight relationship between a collection means which communicates with a body cavity for receiving fluids therefrom, and a suction means which creates a negative pressure within the collection means and removes the gases from the body fluids received in the collection means. The control module includes an entrance port to permit gases to enter the control module from the collection means, an exit port to permit the gases to exit from the control module to the suction means, gas-preventing return means disposed between the entrance port and the exit port to prevent a return of gases to the collection means, and suction control means disposed between the gas-preventing return means and the exit port to regulate the amount of negative pressure applied to the collection means by the suction means.

In a preferred embodiment, the module further includes a liquid-filled air leak indicator means disposed between the entrance port and gas-preventing return means. Bubbles observed in the liquid are indicative of the flow of gases from the collection means to the suction means. Baffle means are disposed both upstream and downstream of the indicator liquid to prevent the liquid from leaving the air leak indicator means and reaching either the gas-preventing return means or any other system control means in the module if the drainage device is tipped in any direction. In addition, the control module includes positive pressure relief means, negative pressure relief means, applied suction indicating means, and system pressure indicator means.

Thus, all of the system control components are provided in a unitary control module. The control module can be used with many different bottles and the bottles can be made of a much simpler and less expensive design. The concept of nesting the module in an external recess in the collection container enables the profile of the system to be substantially reduced.

BRIEF DESCRIPTION OF THE DRAWINGS

FIG. 3 is a top, partial sectional view taken along the section lines 3—3 of FIG. 2, showing some of the system control valve and indicator means.

FIG. 4 is a top, sectional view taken along the section lines 4—4 of FIG. 2, showing the upper chambers above the platform.

FIG. 5 is a top, sectional view taken along the section lines 5—5 of FIG. 2, showing the lower chambers below the platform.

DETAILED DESCRIPTION OF A PREFERRED EMBODIMENT

Figure 1:
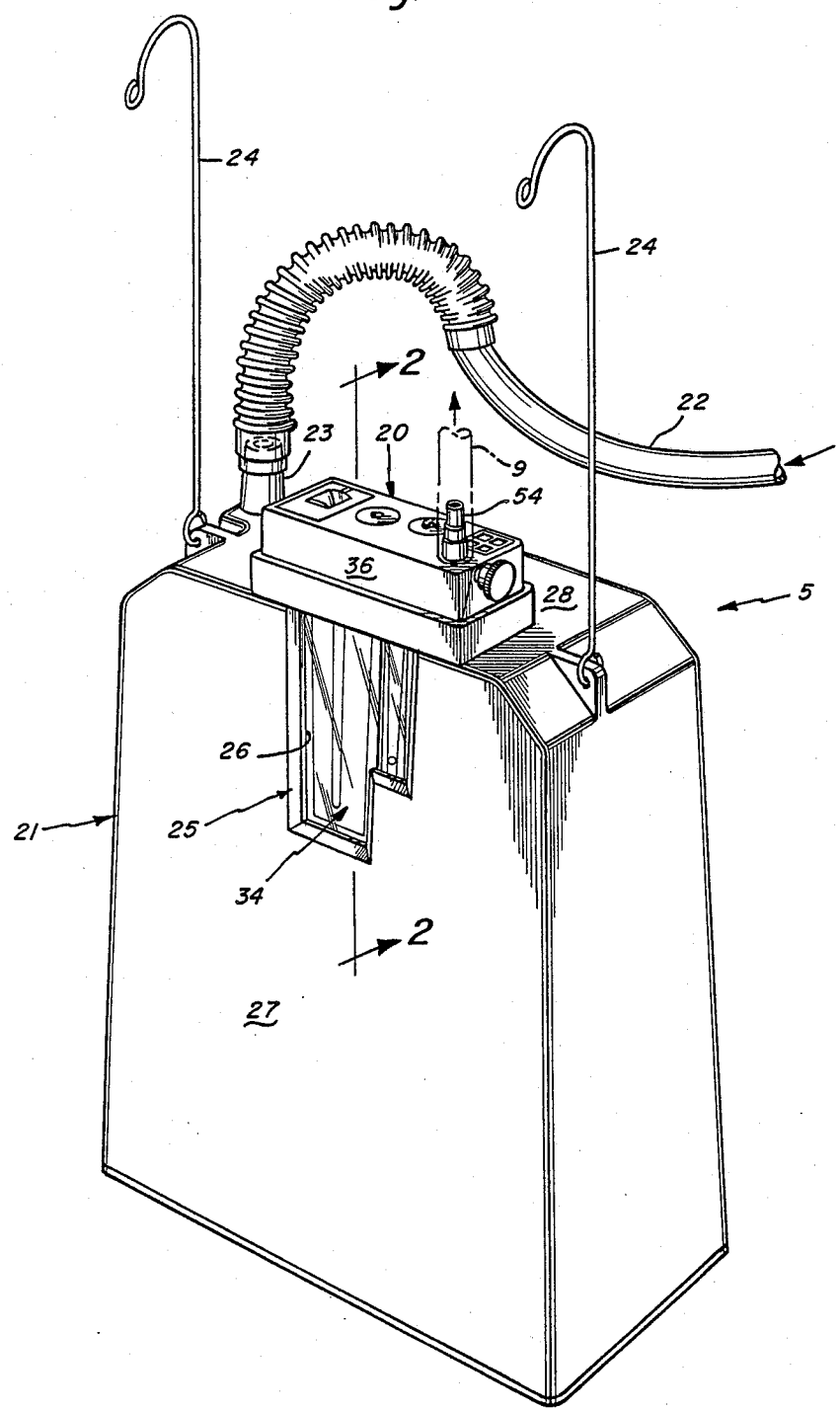
FIG. 1 is a perspective view of the control module of this invention connected to a collection container.

The thoracic drainage device 5 of this invention is shown in FIG. 1. The device includes a control module 20 connected to a collection container 21. Container 21 is substantially rectangular having outside walls which define and lie within a three-dimensional envelope. Internal walls of the container define an externally facing recess 25 within the envelope which is adapted to receive control module 20 and to enable the module to nest within the recess. The control module is shaped so that at least a major portion of the module is contained within the envelope. The collection bottle and control module are made of a nontoxic, injection moldable plastic such as styrene.

A flexible tube 22 for transmitting body fluids (liquids and gases) from the body cavity to the collection means is connected at one end to the body cavity and at the opposing end in airtight engagement to a tubular projection 23 extending from the top wall 28 of the collection container. The liquids from the body cavity are retained in the collection container 21, but the gases flow out the container, through the control module, and out the exit port 54 on top of the control module via a tube 9 to a suction source (not shown). A pair of elongated metal hooks 24 extend from opposing sides of the collection container for hanging the device on a bedrail or, by hooking the two hooks together to provide a handle, for carrying the device by hand.

The control module 20 contains all of the system control means for regulating the flow of gas through and for controlling the gas pressure in the thoracic drainage device. None of the system control means are carried in the container. The control module includes a lower housing 34 and an upper housing 36. Lower housing 34 sits within the complimentary-shaped recess 25 in the outside front wall 27 of the collection container, as shown in FIG. 1. The recess 25 extends to the top wall 28 of the collection container, and upper housing 36 of the control module lies above top wall 28 of the collection container. A flange 26 extending around the front edge of the lower housing fits within a complimentary-shaped groove in the collection container to securely position the control module on the collection container.

Figure 10:
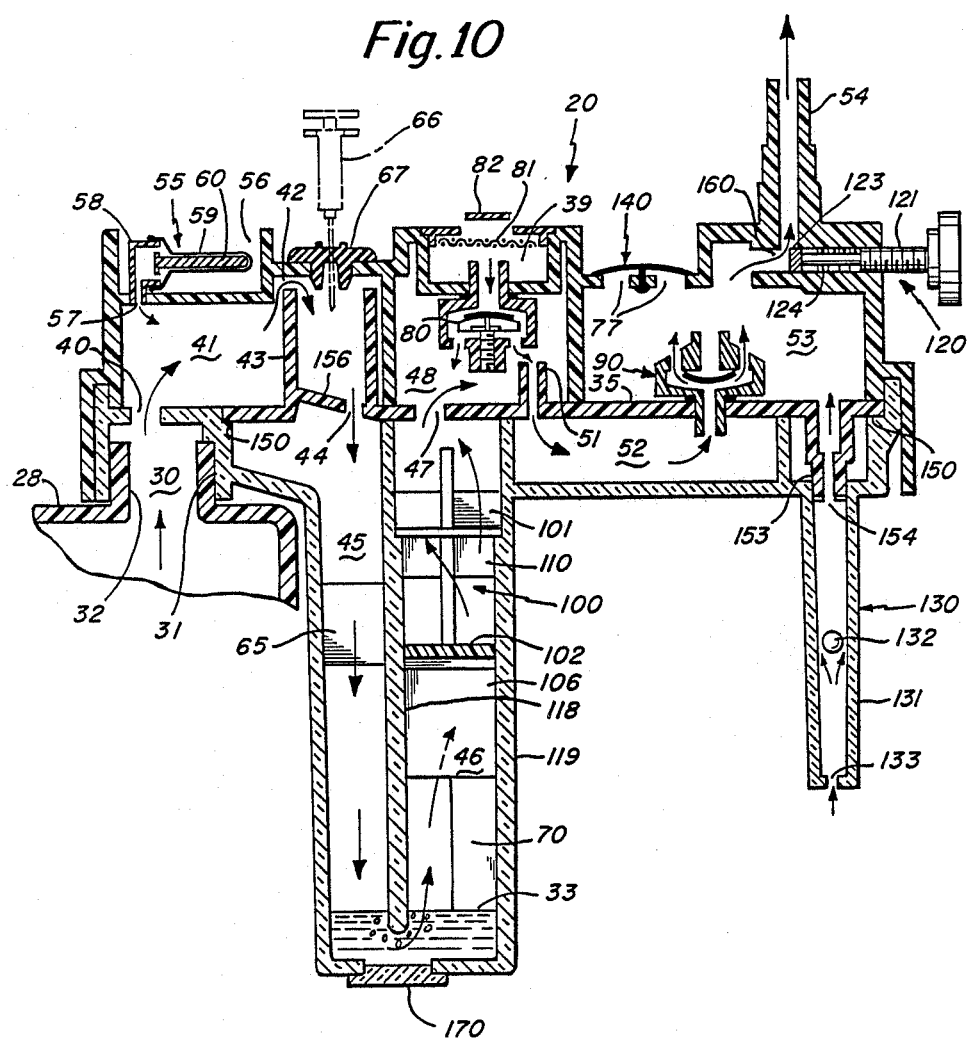
FIG. 10 is an illustrative front, sectional view showing the flow path of gases through the control module.

As shown in FIG. 10, a single airtight fluid connection exists between the control module and collection container at the inlet or entrance port 30 to the control module. The gases from the body fluids collect in an air space above the liquids in the collection container and pass out of an aperture in the top wall 28 of the container through port 30 into the control module. A downwardly extending tubular projection 31 on the control module fits snugly around a mating upwardly extending tubular projection 32 on the collection container to form port 30. The connection is rendered airtight by solvent bonding the plastic projections 31 and 32 together. In a preferred embodiment, both the collection container and control module may be made of styrene and may be bonded with the solvent methyl ethyl ketone. Further, a baffle means (not shown) may be provided at this connection to prevent foam from entering the control module. Alternatively, a standard screw adaptor (not shown) may be disposed at the control module entrance port to facilitate connection to the collection container.

Typically, different size collection containers are provided for adults, children, and infants. The control module of this invention can be connected to any size collection container, bottle, or chamber. Furthermore, the control module is useful for devices other than thoracic drainage, such as an autotransfusion unit or any device which requires a closed and regulated suction system. In addition, a multiplicity of entrance ports may be provided on a single control module for connection to a plurality of collection means.

By fitting the control module within a complimentary-shaped recess in the collection means, the overall height of the unit can be substantially reduced. By way of example, the control module shown in FIG. 1 may be 5.25 inches in height, 4.75 inches in width, and 2.25 inches in thickness, and the collection container may be 8.85 inches in height, 7.50 inches in width, 4.0 inches in thickness and hold 2,500 cc. The upper housing 36 in this example extends 1.9 inches above the top of the collection container. Thus, the combined collection container and control module is less than 12 inches in height and can be readily carried on a bedrail.

Figure 9:
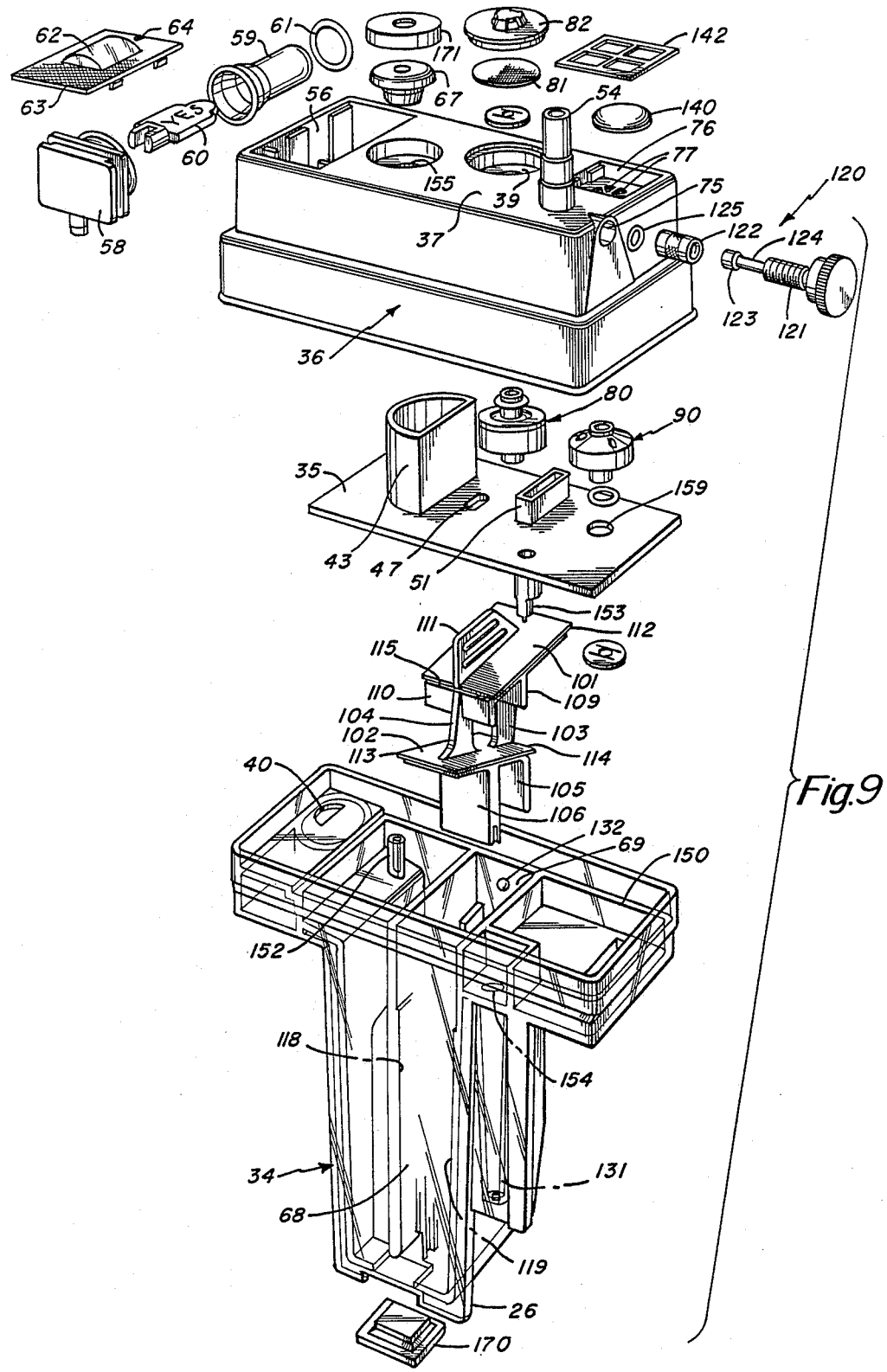
FIG. 9 is an exploded, perspective view of the control module showing the various system components.

As shown in FIG. 9, the control module consists of an optically-clear lower housing 34, an upper housing 36, a platform 35 between the upper and lower housings, and a plurality of valves, baffle and indicator means for controlling and monitoring the flow of gases through the thoracic drainage device. The upper and lower housings and platform are made of impact-resistant plastic such as styrene. The upper and lower housings are glued or sonically welded together at mating edges to provide an airtight connection.

The platform 35 lies between the upper and lower housings and separates the lower chambers 45, 46, 52 (see FIG. 10) in the lower housing from the upper chambers 41, 48, 53 in the upper housing. The platform 35 rests on a ledge 150 extending around and adjacent the top edge of the lower housing. A pin 151 (FIG. 2) extending downwardly from the lower surface of the platform fits within a mating tubular projection 152 in the lower housing to position the platform on the lower housing. Further, a tubular projection 153 extending downwardly from the lower surface of the platform fits snugly within a mating aperture 154 in the lower housing to form an airtight fluid connection as discussed hereinafter.

As best shown in FIG. 10, the control module comprises a plurality of chambers disposed in serial arrangement forming an internal passageway between the entrance port 30 and the exit port 54. Gases from the collection container flow through the entrance port 30 and restricted aperture 40 into a first chamber 41 of the module. A system pressure indicator 55 is connected to the first chamber via aperture 57 for indicating whether the gases in the collection container are under negative pressure. The gases flow from the first chamber 41 through an aperture 42 at the top of the first chamber, down a funnel 43 extending upwardly from the platform 35, through an aperture 44 in the platform and down into a second chamber 45 below the platform. The gases flow through a liquid 33 disposed at the adjoining bottoms of the second chamber 45 and a third chamber 46, and up through the third chamber. The second and third chambers 45, 46 form the upstream and downstream legs respectively of an air leak indicator. A convoluted baffle means 100 is provided at the upper end of the third chamber to prevent loss of the air leak indicator liquid 33 if the device is tipped in any direction. The gases flow through the baffle means 100, through an aperture 47 in the platform, and into a fourth chamber 48 above the platform. A high negative pressure relief means 80 is connected to the fourth chamber. The gases flow out of the fourth chamber via an aperture 51 in the platform and down into a fifth chamber 52 below the platform. The gases then flow through a dry one-way seal means 90 disposed in an aperture in the platform to a sixth chamber 53 above the platform. Connected to the sixth chamber are a positive pressure relief means 140, a suction control means 120, and a suction indicator means 130. The gases exit the sixth chamber at exit port 54 to the suction means via a tube connected in airtight relationship to exit port 54.

Figure 7:
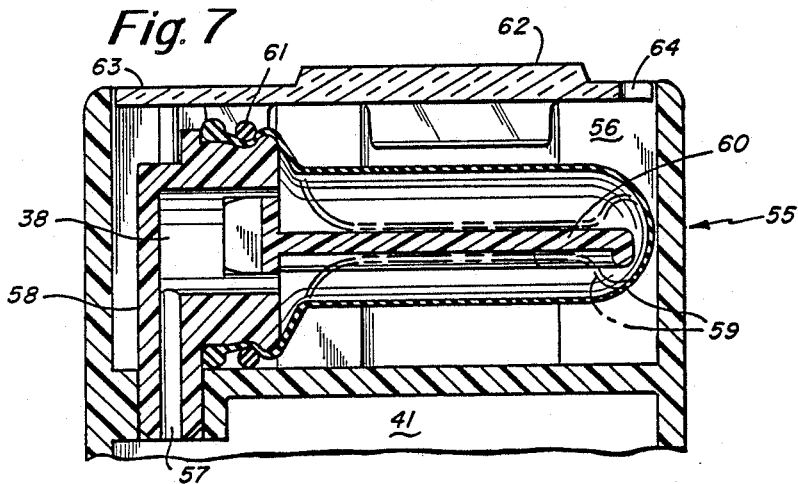
FIG. 7 is a fragmentary side, sectional view taken along the section lines 7—7 of FIG. 2, showing the system pressure indicator in cross-section.

The system pressure indicator (SPI) 55, shown in detail in FIG. 7, is disposed in a recess 56 in the top wall 37 of the upper housing and is connected to the first chamber 41 via an aperture 57 in the top wall of the first chamber. The SPI includes a right angle support member 58, an elastomeric membrane 59, and a sign means 60. The gases which enter the SPI from the first chamber are at the same pressure as the gases in the collection container and thus the SPI provides, via the sign means, a visual indication of whether the pressure in the collection container is negative or positive. The gases from the first chamber flow through the right angle bore 38 of support member 58 and into the tubular elastomeric membrane 59 which is closed at its distal end and sealed by an O-ring 61 at its proximal end about one end of the support member. Also mounted to the support member and positioned within the elastomeric membrane is the sign means 60 bearing the letters "YES" to indicate negative pressure. A magnifying lens 62 is mounted in a cover panel 63 which is disposed above the membrane on the upper housing so that the elastomeric membrane is visible through the lens. An aperture 64 in the cover panel permits atmospheric air to enter the recess 56. When the gases within the collection chamber are at negative pressure, the elastomeric membrane collapses due to the higher atmospheric pressure on the outside of the membrane. In the collapsed state, the sign bearing the term "YES" is visible through the membrane. This indicates to the attending medical personnel that the collection container is under negative pressure, as desired. If the pressure in the collection container is positive, the membrane will expand and the words "YES" will not be visible. This will indicate to the attending medical personnel that the pressure in the collection container is positive and corrective action can then be taken.

From the first chamber 41 the gases flow through a small aperture 42 formed between the top edge of funnel 43 and the top wall 37 of the upper housing. The gases flow through the funnel 43, and out a small aperture 44 in the bottom wall of the funnel and into a second chamber 45 comprising the upstream leg of the air leak indicator. The lower end of the second chamber and the adjoining lower end of the third chamber form a U-tube which is filled with about 15–20 cc's of saline or other suitable liquid 33. The liquid is injected via a syringe 66 through a resealable rubber stopper 67 disposed in an aperture 155 in the top wall 37 of the upper housing and the liquid flows through the funnel to the bottom of the second chamber. Cover 171 helps maintain the stopper in position and has a central aperture for guiding the syringe needle through the center of the stopper. The air leak indicator liquid 33 can be drained via the removable closure 170 at the bottom of the air leak indicator.

Because the lower housing 34 is transparent, the air leak indicator liquid 33 is visible in the U-tube defined by chambers 45, 46. Gases exiting the pleural cavity and collection container are visible as they bubble through the indicator liquid in the bottom of the U-tube. The attending medical personnel use this visual indication of gases moving through the indicator liquid from the upstream leg 45 to the downstream leg 46 to confirm that an intrapleural air leak exists and to verify that the gases are moving in the correct direction, i.e., out of the patient and to the suction source. A ball 158 (FIG. 2), coated with a dissolvable dye, may be placed in the air leak indicator to color the liquid 33 which aids in observing the gas flow through the liquid.

Baffle means are provided both upstream and downstream of the indicator liquid to prevent the liquid from escaping the air leak indicator and contaminating the other components of the control module if the device is tipped up to 90° in any direction. Upstream of the indicator liquid, the two small apertures 42 and 44, the funnel 43 having slanted bottom wall 156, and the slanted drainage wall 65 at the upper end of the second chamber, insure that the liquid does not reach the first chamber if the device is tipped in any direction.

Figure 8:
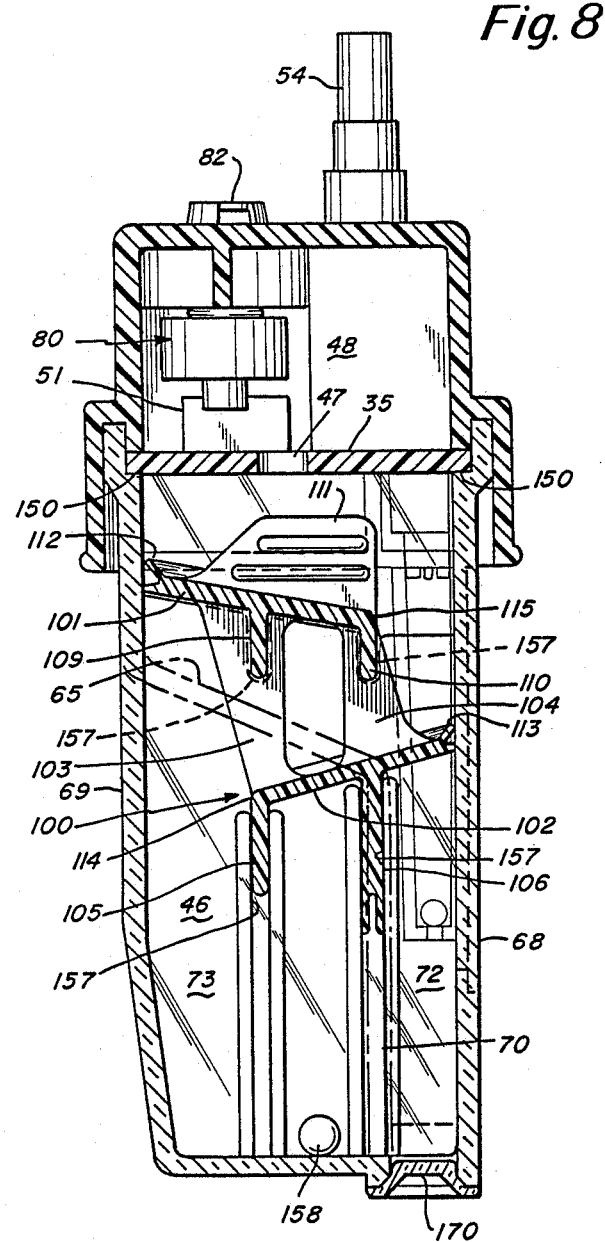
FIG. 8 is a side, sectional view taken along the section lines 8—8 of FIG. 2.

The baffle means 100 inserted into the upper portion of the downstream leg 46 of the air leak indicator provides a tortuous path to prevent the indicator liquid 33 from leaving downstream leg 46 if the device is tipped in any direction. As shown in FIGS. 8 and 9, the baffle means 100 consists of an upper baffle wall 101 slanting downwardly in the forward direction, a lower baffle wall 102 slanting downwardly in the rear direction, a pair of vertical connecting members 103, 104 joining the upper and lower baffle walls, a vertical gripping portion 111 extending upwardly from the upper baffle wall, a pair of vertical upper splash guards 109, 110 extending downwardly from the upper baffle wall, a pair of vertical lower splash guards 105, 106 extending downwardly from the lower baffle wall, and resilient edge flanges 112, 113 on the edges of the upper and lower baffle walls respectively.

The baffle means 100 preferably is formed in a single piece which is insertable into the third chamber 46 of the module. The third chamber is substantially rectangular and consists of a front wall 68, a rear wall 69, and opposing sidewalls 118 and 119. By holding the gripping portion 111, the baffle means 100 is inserted into the upper portion of the third chamber. Upper baffle wall 101 is shaped to extend between the chamber sidewalls 118, 119 and from the rear chamber wall 69 to a front edge 115 of the upper baffle wall which is disposed at a point short of the front chamber wall 68 to form a front passageway between the edge 115 and the front chamber wall 68. Lower baffle wall 102 is shaped to extend between the chamber sidewalls 118, 119 and from the front chamber wall 68 to a rear edge 114 positioned short of the rear chamber wall 69 to form a rear passageway between the edge 114 and the rear chamber wall 69. Resilient flanges 112 and 113 are provided on the outer edges of the upper and lower baffle walls respectively, except for front edge 115 and rear edge 114 which do not contact the chamber walls. The baffle means is pushed downwardly into the third chamber so that the resilient flanges 112 and 113 are press-fit against the inner walls of the third chamber to form a liquid-tight seal between the baffle walls and third chamber walls. Furthermore, the side edges of splash guards 105, 106, 109 and 110 are pushed into complimentary-shaped grooves 157 on the inner walls of the third chamber to hold the baffle means securely in place.

Figure 2:
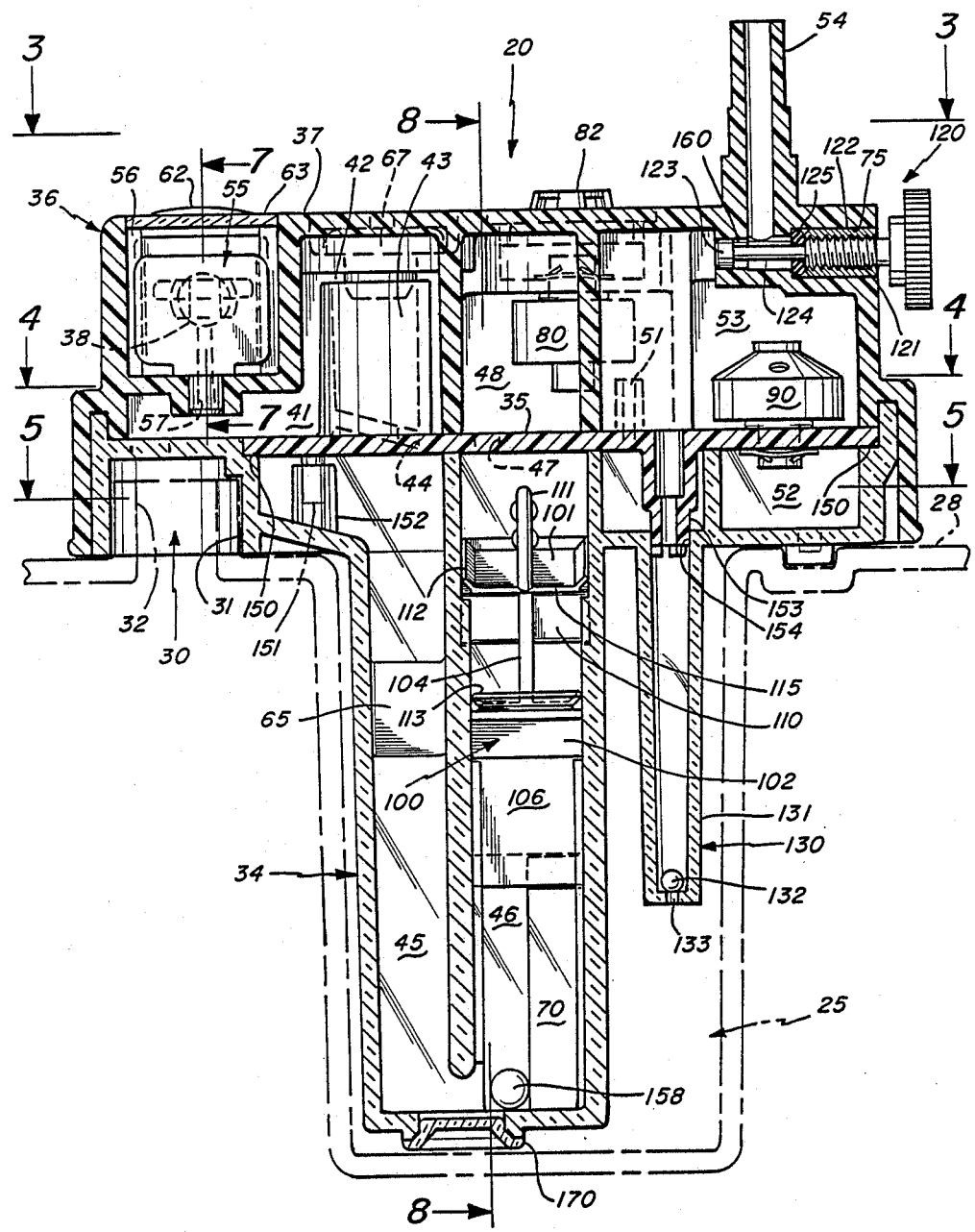
FIG. 2 is a front, sectional view of the control module taken along the section lines 2—2 of FIG. 1.
Figure 6:
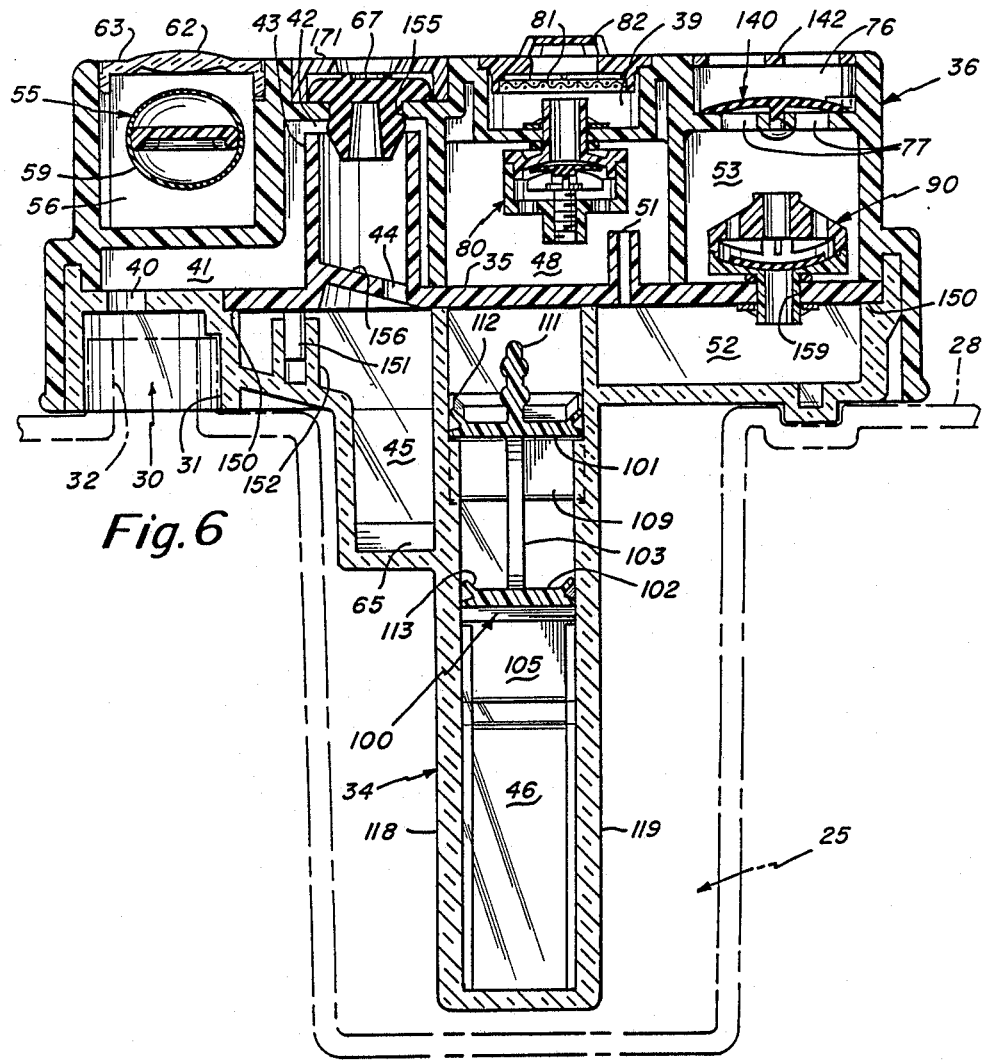
FIG. 6 is a front, sectional view taken along the section lines 6—6 of FIG. 3, showing a number of the system control means in cross-section.
Figure 11:
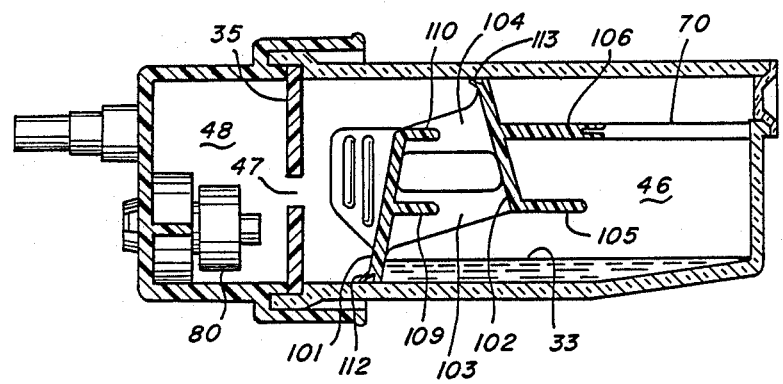
FIG. 11 is an illustrative side, sectional view of the control module in a tilted position to show how the baffle means prevent loss of the air leak indicator liquid.

As shown in FIGS. 2 and 8, an interior wall 70, extending from below splash guard 106 to the bottom of the third chamber and partially across the third chamber, divides the lower portion of the third chamber into a front portion 72 and a rear portion 73 to inhibit the flow of the indicator liquid 33 to the rear portion 73. Thus, in order for the indicator liquid 33 to exit the third chamber, it must travel first to the rear portion 73, up and through the second passageway formed by rear lower baffle wall edge 114 and rear chamber wall 69, between the upper and lower baffle walls 101, 102, up and through the first passageway defined by front upper baffle wall edge 115 and front chamber wall 68, and above the upper baffle wall 101 through the narrow aperture 47 disposed in the center of the top wall of the third chamber. As shown in FIG. 11, when the device is tipped up to 90° in any direction, the splash guards 105, 106, 109, 110 impede the flow of the indicator liquid 33 out of the third chamber. Further, the upper and lower baffle walls 101, 102 are slanted to facilitate drainage of the indicator liquid back to the bottom of the third chamber. Thus, by providing baffle means 100 in the downstream leg of the third chamber, the indicator liquid cannot escape downstream of the third chamber if the device is tipped up to 90° in any direction. This is important because a dry one-way valve means, whose operation depends upon being dry, is disposed downstream of the air leak indicator as discussed hereinafter.

The gases leaving the third chamber pass through aperture 47 and enter the fourth chamber 48. A high negative pressure relief valve 80 is disposed in a recess 39 in the top wall of the upper housing and communicates with the gases in the fourth chamber. The high negative pressure relief valve is an adjustable one-way mechanical valve which is set and calibrated to open automatically to allow air to enter the fourth chamber if the pressure in that chamber falls below a predetermined negative pressure, e.g., $-45$ cm $H_2O$. For example, when the patient tube is stripped to remove clots or obstructions in the tube, there is usually a sharp increase in negative pressure in the control module. Further, if the suction regulator means 120 were to malfunction, there might be an increase in negative pressure. In these cases, the excess negative pressure is automatically relieved by the introduction of air via the high negative relief valve. An anti-bacteria filter 81 is disposed above the valve to prevent contamination of the module by the incoming air. A vented cap 82 is provided for retaining in position and protecting filter 81.

The gases in the fourth chamber exit through an upstanding conduit 51, extending upwardly from the platform, to a fifth chamber 52 below the platform. In the unlikely event that liquid entered the fourth chamber 48, the conduit 51 prevents any liquid from reaching the fifth chamber 52. Disposed at the exit aperture 159 in the top wall of the fifth chamber 52 is a gas-preventing return means such as a one-way mechanical valve 90 which permits gases to exit the fifth chamber but prohibits them from re-entering the fifth chamber. This one-way seal protection is essential to prevent gases in the control module from re-entering the pleural cavity which could enable positive pressure to build up in the pleural cavity and result in a potentially dangerous situation. The one-way valve 90 is typically set to open at about 1 to 1.5 cm $H_2O$.

The gases which enter the sixth chamber 53 via the one-way valve are in communication with the suction source, a suction control means 120, a suction level indicator 130, and a positive pressure relief valve 140. The suction source, such as a hospital wall suction source or a portable suction means, is connected via a tube to the exit port defined by tubular conduit 54. Because the hospital wall unit or suction source may be set at an excessive level of suction, suction control means 120 are provided to limit the amount of suction provided by the source to the collection container. The suction control means consists of a screw/rotameter combination which will regulate the pressure in the collection container to the normally desirable levels of vacuum, e.g., 0–40 cm of $H_2O$. A regulator screw 121 has a tapered plug 123 at its distal end which is positionable across the exit aperture 160 of the sixth chamber to regulate the flow of gas between sixth chamber 53 and conduit 54. As shown in FIGS. 2 and 10, the screw is threaded into a brass insert 122 disposed in a bore 75 in the top housing. Plug 123 is tapered at the distal end and exit bore or aperture 160 adjoins a larger diameter section beneath conduit 54 so that movement of the tapered plug end across aperture 160 permits precise control of the level of applied suction. An O-ring 125 limits the extent to which the screw 121 can be unscrewed and forms a seal between the bore and a reduced diameter section 124 of the screw to prevent air leakage.

A visual indication of the level of applied suction is provided by a suction indicator flow tube 131 and flow ball 132 in communication with the sixth chamber. Tubular conduit 153 extending downwardly from platform 35 connects the flow tube 131 to the sixth chamber. An aperture 133 in the bottom of the flow tube allows atmospheric air to enter the bottom of the tube and the difference in pressure between the gas in the sixth chamber and atmospheric pressure causes the ball 132 to rise in the transparent tube 131 wherein the amount of rise is proportional to the pressure difference and may be indicated by a calibrated scale on the flow tube. The flow tube 131 is positioned adjacent the front wall of the control module, alongside the air leak indicator, so that both are readily visible when the control module is positioned in recess 25 in the collection container.

The positive pressure relief valve 140, consisting of a single mushroom valve, is disposed in a recess 76 in the top wall 37 of the upper housing and is in communication with the gases in the sixth chamber via a plurality of apertures 77 in the bottom of the recess. If positive pressure builds up within the control module, such as when the patient coughs, the positive pressure relief valve will open automatically to allow gases to escape from the control module. A grid 142 is provided above the valve to prevent injury to or tampering with the valve.

Thus, all of the necessary system components for regulating the flow of gases through a suction drainage device have been provided in a compact modular control unit. Although the preferred embodiment of the invention has been described, it will be appreciated that variations of the invention will be perceived by those skilled in the art, which variations are nevertheless within the scope of the invention as defined by the claims appended hereto.

What is claimed is:

1. A control module for regulating the flow of gases in a suction drainage apparatus of the type having a collection container in communication with a body cavity to receive body fluids (including liquids and gases) from the body cavity and a suction source for creating a negative pressure within the collection container and removing the gases of the body fluids, said control module comprising:

an entrance port connectable in airtight relationship to the collection container to permit the gases of the body fluids to enter said control module from said collection container;

an exit port connectable in airtight relationship to the suction means to permit the gases to exit said a control module to said suction means; and all of the control means for the suction drainage apparatus being carried by said module and none by the container whereby the module may be used with different configurations of containers, said control means comprising:

gas-preventing return means disposed between said entrance port and said exit port to prevent the return of gases to said collection container after being removed therefrom by said suction means;

air leak indicator means disposed between said entrance port and said gas-preventing return means adapted to receive an indicator liquid for observing the gases flowing from said collection container to said suction means;

baffle means disposed on both sides of said air leak indicator means to prevent the indicator liquid from leaving said air leak indicator means if the drainage apparatus is tipped up to 90° in any direction; and suction control means disposed between said gas-preventing return means and said exit port to regulate the amount of negative pressure applied to said collection container by said suction means.

2. The control module of claim 1, said control means further comprising:

positive pressure relief means for relieving any build up of positive pressure in the control module.

3. The control module of claim 2, said control means further comprising:

negataive pressure relief means for relieving excess negative pressure in the control module.

4. The control module of claim 3, said control means further comprising:

suction level indicator means disposed between said gas-preventing return means and said exit port for indicating the amount of suction applied by said suction means as regulated by said suction control means.

5. The control module of claim 4, said control means further comprising:

system pressure indicator means disposed between said entrance port and said air leak indicator means for indicating whether the pressure in said collection container is negative.

6. The control module of claim 1, wherein said control module is shaped to fit within a complimentary-shaped recess in the collection container.

7. A control module for regulating the flow of gases in a suction drainage apparatus of the type having a collection container in communication with a body cavity to receive body fluids (including liquids and gases) from the body cavity and a suction source for creating a negative pressure within the collection container and removing the gases of the body fluids, said control module comprising:

an entrance port connectable in airtight relationship to the collection container to permit the gases of the body fluids to enter said control module from said collection container;

an exit port connectable in airtight relationship to the suction means to permit the gases to exit said control module to said suction means;

six chambers connected serially between said entrance port and said exit port, said chambers of said module containing all of the control means for the suction drainage apparatus and none being carried by the container whereby the module may be used with different configurations of containers;

a first of said six chambers including a system pressure indicator for indicating whether the pressure in said collection container is negative;

a second and third of said six chambers comprising the upstream and downstream legs respectively of an air leak indicator means adapted to receive an indicator liquid for observing the gases flowing from said collection container to said suction means;

a fourth of said six chambers including a negative pressure relief means for relieving excess negative pressure in the collection container;

a fifth and sixth of said six chambers being connected by a gas-preventing return means to prevent the return of gases to said collection container after being removed therefrom by said suction means;

and said sixth chamber including a suction control means for regulating the amount of negative pressure applied to said collection container by said suction means.

8. The control module of claim 7, said control means further comprising:

baffle means disposed in said upstream and downstream legs to prevent the indicator liquid from leaving the air leak indicator means if the apparatus is tipped up to 90° in any direction;

a positive pressure relief means connected to said sixth chamber for relieving any buildup of positive pressure in the control module; and a suction level indicator connected to said sixth chamber for indicating the amount of suction applied by said suction means as regulated by said suction control means.

9. The control module of claim 8 wherein said gas-preventing return means is a one-way mechanical valve.

10. A thoracic suction drainage system having a collection container and a control module for regulating gas flow and pressures in the system comprising:

a collection container having outside walls which define and lie within a three-dimensional envelope and internal wall means defining an externally facing three-dimensional recess within the envelope, the recess being adapted to receive a control module and to enable the module to nest within the recess;

said control module having system control means for controlling the gas flow through and for controlling the gas pressure in the container;

all of the control means for said system being carried by the module and none being carried by the container whereby the module may be used with different configurations of containers;

said module being nested within the recess and being dimensioned and shaped so that at least a major portion of the module is contained within said envelope;

said control module further comprising:

an inlet port connectable to the interior of the collection container to permit gas to enter the module from the container;

an exit port connectable to a source of suction; internal passageway means extending through the module from the inlet port to the exit port; and said control means comprising:

one-way valve means disposed along the internal passageway means to permit the flow of gas to the exit port but to prevent the flow of gas in a reverse direction;

suction control means disposed between the one-way valve means and the exit port to regulate the degree of suction applied to the container; and air leak indicator means disposed along the internal passageway means, said air leak indicator means being located so that when the module is nested in the recess the air leak indicator means will be exposed externally.

11. A thoracic drainage system having a collection container and a control module for regulating gas flow and pressures in the system comprising:

a control module having an inlet port connectable to the interior of a collection container to permit gases to enter the module from the container, an exit port connectable to a source of suction, and means defining an internal passageway means extending from the inlet port to the exit port;

said control module including all of the control means for the thoracic drainage system whereby the module may be used with different configurations of containers, said system control means comprising:

one-way valve means disposed along said internal passageway means to permit the flow of gas to the exit port but to prevent the flow of gas in a reverse direction;

suction control means disposed along said internal passageway means between the one-way valve means and the exit port to regulate the degree of negative pressure applied to the container;

air leak indicator means disposed along the internal passageway means and adapted to contain an indicator liquid through which the gases will bubble for observing the flow of gases from the collection container toward the exit port;

positive pressure relief means disposed along said internal passageway means for relieving build up of positive pressure in the system; and high negative pressure relief means disposed along said internal passageway means for relieving excess negative pressure in the system;

said collection container being independent of and carrying no system control means.

12. Baffle means insertable in a rectangular chamber containing liquid and gas for allowing the escape of gas but not liquid from the chamber and for preventing the loss of liquid from the chamber if the chamber is tipped in any direction, said chamber consisting of a bottom wall, a first pair of opposing sidewalls, and a second pair of opposing sidewalls comprising a front wall and a rear wall, said baffle means comprising:

an upper baffle wall having three edges in contact with the first pair of chamber sidewalls and the rear chamber wall respectively and a fourth front edge spaced from the front chamber wall to form a first passageway between the front chamber wall and the fourth front edge, the upper baffle wall slanting downwardly toward the fourth front edge;

a lower baffle wall disposed below the upper baffle wall, said lower baffle wall having three edges in contact with the first pair of chamber sidewalls and the front chamber wall respectively and a fourth rear edge spaced from the rear chamber wall to form a second passageway between the rear chamber wall and the fourth rear edge, the lower baffle wall slanting downwardly toward the fourth rear edge;

means for connecting the upper and lower baffle walls and allowing gas to escape therebetween;

resilient flanges on each of the three edges of the upper and lower baffle walls to form a press-fit liquid-tight seal between the flanges and the chamber walls which they contact; and retainer flaps extending downwardly from each of the fourth front and fourth rear edges of the upper and lower baffle walls respectively for retarding the flow of liquid from the chamber if the chamber is tipped in any direction.

* * * * *